US009535018B2

(12) United States Patent
Peterlinz et al.

(10) Patent No.: US 9,535,018 B2
(45) Date of Patent: Jan. 3, 2017

(54) COMBINED X-RAY AND OPTICAL METROLOGY

(71) Applicant: KLA-Tencor Corporation, Milpitas, CA (US)

(72) Inventors: Kevin A. Peterlinz, Fremont, CA (US); Andrei V. Shchegrov, Campbell, CA (US); Michael S. Bakeman, San Jose, CA (US); Thaddeus Gerard Dziura, San Jose, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 482 days.

(21) Appl. No.: 14/074,689

(22) Filed: Nov. 7, 2013

(65) Prior Publication Data

US 2015/0032398 A1 Jan. 29, 2015

Related U.S. Application Data

(60) Provisional application No. 61/867,363, filed on Aug. 19, 2013, provisional application No. 61/843,868, filed on Jul. 8, 2013.

(51) Int. Cl.
*G01N 23/203* (2006.01)
*G01B 15/00* (2006.01)
(Continued)

(52) U.S. Cl.
CPC .............. *G01N 23/203* (2013.01); *G01B 15/00* (2013.01); *G01N 23/2206* (2013.01);
(Continued)

(58) Field of Classification Search
CPC . G01B 15/00; G01B 2210/56; G01N 23/2206; G01N 23/203; G01N 21/00; H01L 22/12; H01L 22/20
(Continued)

(56) References Cited

U.S. PATENT DOCUMENTS 5,420,436 A 5/1995 Seya et al.
6,079,876 A 6/2000 Schuetz
(Continued)

OTHER PUBLICATIONS

International Search Report and Written Opinion mailed on Oct. 28, 2014, for PCT Application No. PCT/US2014/045607 filed on Jul. 7, 2014, by KLA-Tencor Corporation, 10 pages.
(Continued)

*Primary Examiner* — Carol S Tsai
(74) *Attorney, Agent, or Firm* — Spano Law Group; Joseph S. Spano

(57) ABSTRACT

Structural parameters of a specimen are determined by fitting models of the response of the specimen to measurements collected by different measurement techniques in a combined analysis. X-ray measurement data of a specimen is analyzed to determine at least one specimen parameter value that is treated as a constant in a combined analysis of both optical measurements and x-ray measurements of the specimen. For example, a particular structural property or a particular material property, such as an elemental composition of the specimen, is determined based on x-ray measurement data. The parameter(s) determined from the x-ray measurement data are treated as constants in a subsequent, combined analysis of both optical measurements and x-ray measurements of the specimen. In a further aspect, the structure of the response models is altered based on the quality of the fit between the models and the corresponding measurement data.

20 Claims, 5 Drawing Sheets

(51) Int. Cl.
*G01N 23/22* (2006.01)
*H01L 21/66* (2006.01)

(52) U.S. Cl.
CPC .......... *G01B 2210/56* (2013.01); *H01L 22/12* (2013.01); *H01L 22/20* (2013.01)

(58) Field of Classification Search
USPC ......... 702/81, 189; 703/1; 356/72, 331–334; 378/84, 86, 85, 145, 156, 159; 250/503.1, 250/8–10, 68, 129–132
See application file for complete search history.

(56) References Cited

U.S. PATENT DOCUMENTS

| | | | |
|---|---|---|---|
| 6,633,831 B2 | 10/2003 | Nikoonahad et al. | |
| 6,765,205 B2 | 7/2004 | Ochiai et al. | |
| 6,816,570 B2 | 11/2004 | Janik et al. | |
| 6,888,918 B2 | 5/2005 | Horai et al. | |
| 7,072,442 B1 | 7/2006 | Janik | |
| 7,305,066 B2 * | 12/2007 | Ukita | H01J 35/28 378/126 |
| 7,456,399 B1 | 11/2008 | Soderstrom | |
| 7,478,019 B2 | 1/2009 | Zangooie et al. | |
| 7,826,071 B2 | 11/2010 | Shchegrov et al. | |
| 7,929,667 B1 | 4/2011 | Zhuang et al. | |
| 7,991,116 B2 * | 8/2011 | Chen | B82Y 10/00 250/503.1 |
| 8,076,654 B2 | 12/2011 | Hatakeyama et al. | |
| 8,982,338 B2 * | 3/2015 | Hamilton | G01N 23/223 356/72 |
| 2002/0070365 A1 | 6/2002 | Karellas | |
| 2003/0113006 A1 | 6/2003 | Berestov | |
| 2012/0045855 A1 | 2/2012 | Beck et al. | |
| 2013/0009122 A1 | 1/2013 | Park et al. | |
| 2013/0304424 A1 * | 11/2013 | Bakeman | G03F 7/70625 702/189 |
| 2013/0321793 A1 * | 12/2013 | Hamilton | G01N 23/223 356/72 |
| 2014/0019097 A1 * | 1/2014 | Bakeman | G06F 17/5068 703/1 |

OTHER PUBLICATIONS

Inventor(s): R.M. Silver et al. Title: Improving Optical Measurement Accuracy using Multi-Technique Nested Uncertainties Proc. of SPIE vol. 7272 727202-3.
D.K. Bowen and B.K. Tanner "X-ray Metrology in Semiconductor Manufacturing", CRC Press, 2006.
Inventor(s): W. Kim et al. Title: Extended Scalability of Perpendicular STT-MRAM Towards sub 20-nm MTJ Node Source: IEDM-11, pp. 531-534 Date: 2011.

* cited by examiner

COMBINED X-RAY AND OPTICAL METROLOGY

CROSS REFERENCE TO RELATED APPLICATIONS

The present application for patent claims priority under 35 U.S.C. §119 from U.S. provisional patent application Ser. No. 61/867,363, entitled "Method of Measuring Semiconductor Structure Parameters Using Optical and X-Ray Absorbance-Emission Metrology Technologies," filed Aug. 19, 2013, and from U.S. provisional patent application Ser. No. 61/843,868, entitled "Model Building, Analysis Engine, and Methods for Measuring Semiconductor Film and Structure Parameters on Device Using Optical and X-ray Metrology Technologies Capable of Direct Elemental Detection," filed Jul. 8, 2014, the subject matter of which is incorporated herein by reference in its entirety.

TECHNICAL FIELD

The described embodiments relate to metrology systems and methods, and more particularly to methods and systems for improved measurement accuracy.

BACKGROUND INFORMATION

Semiconductor devices such as logic and memory devices are typically fabricated by a sequence of processing steps applied to a specimen. The various features and multiple structural levels of the semiconductor devices are formed by these processing steps. For example, lithography among others is one semiconductor fabrication process that involves generating a pattern on a semiconductor wafer. Additional examples of semiconductor fabrication processes include, but are not limited to, chemical-mechanical polishing, etch, deposition, and ion implantation. Multiple semiconductor devices may be fabricated on a single semiconductor wafer and then separated into individual semiconductor devices.

Metrology processes are used at various steps during a semiconductor manufacturing process to detect defects on wafers to promote higher yield. Optical metrology techniques offer the potential for high throughput without the risk of sample destruction. A number of optical metrology based techniques including scatterometry and reflectometry implementations and associated analysis algorithms are commonly used to characterize critical dimensions, film thicknesses, composition and other parameters of nanoscale structures.

Traditionally, scatterometry measurements are performed on targets consisting of thin films and/or repeated periodic structures. During device fabrication, these films and periodic structures typically represent the actual device geometry and material structure or an intermediate design. As devices (e.g., logic and memory devices) move toward smaller nanometer-scale dimensions, characterization becomes more difficult. Devices incorporating complex three-dimensional geometry and materials with diverse physical properties contribute to characterization difficulty. For example, modern memory structures are often high-aspect ratio, three-dimensional structures that make it difficult for optical radiation to penetrate to the bottom layers. In addition, the increasing number of parameters required to characterize complex structures (e.g., FinFETs), leads to increasing parameter correlation. As a result, the parameters characterizing the target often cannot be reliably decoupled with available measurements. In another example, opaque, high-k materials are increasingly employed in modern semiconductor structures. Optical radiation is often unable to penetrate layers constructed of these materials. As a result, measurements with thin-film scatterometry tools such as ellipsometers or reflectometers are becoming increasingly challenging.

In response to these challenges, more complex optical tools have been developed. For example, tools with multiple angles of illumination, shorter and broader ranges of illumination wavelengths, and more complete information acquisition from reflected signals (e.g., measuring multiple Mueller matrix elements in addition to the more conventional reflectivity or ellipsometric signals) have been developed. However, these approaches have not reliably overcome fundamental challenges associated with measurement of many advanced targets (e.g., complex 3D structures, structures smaller than 10 nm, structures employing opaque materials) and measurement applications (e.g., line edge roughness and line width roughness measurements).

Another response to these challenges has been the development of metrology tools incorporating multiple measurement technologies. In one example, a thin film analysis system combining grazing incidence x-ray reflectometry with x-ray fluorescence (XRF), as well as electron microprobe analysis is described in U.S. Pat. No. 6,816,570, entitled "Multi-technique thin film analysis tool," issued on Nov. 9, 2004, and assigned to KLA-Tencor Corporation, the subject matter of which is incorporated herein by reference in its entirety.

Future metrology applications present challenges for metrology due to increasingly small resolution requirements, multi-parameter correlation, increasingly complex geometric structures, and increasing use of opaque materials. The use of multiple measurement technologies to characterize a specimen shows promise. However, improvements in the analysis of measurement data generated by multiple measurement technologies is desired.

SUMMARY

Methods and systems for performing measurements of structural and material characteristics (e.g., material composition, dimensional characteristics of structures and films, etc.) associated with different semiconductor fabrication processes are presented. One or more structural parameters of a semiconductor specimen are determined by fitting models of the response of the specimen to measurements collected by different measurement techniques in a combined analysis.

In one aspect, x-ray measurement data of a specimen is analyzed to determine at least one specimen parameter value that is treated as a constant in a combined analysis of both optical measurements and x-ray measurements of the specimen. For example, a particular structural property (e.g., layer thickness, structure volume, etc.), or a particular material property such as an elemental composition of the specimen is determined based on x-ray measurement data. The parameter(s) determined from the x-ray measurement data are treated as constants in a combined analysis of both optical measurements and x-ray measurements of the specimen. This enables increased measurement sensitivity and throughput due to the complementary nature of x-ray and optical techniques. Measurement precision and accuracy can be improved by identifying shared model parameters that are mathematically resolved sequentially or in parallel using data sets derived from x-ray and optical measurements.

Measuring shared parameters with a diversity of measurement technologies reduces correlations among parameters and improves measurement accuracy.

In some embodiments, a model building and analysis engine performs x-ray and optical analyses of common or multiple targets where at least one common parameter is coupled during the analysis.

In a further aspect, the fitting of the optical response model with an amount of optical measurement data and the fitting of the x-ray response model with an amount of x-ray measurement data can be done sequentially, in parallel, or by a combination of sequential and parallel analyses.

In yet another further aspect, the number of floating target parameters of the optical model and the number of floating target parameters of the x-ray model are reduced by linking some of the parameters. In some examples, common geometric parameters are treated as a single parameter. In some other examples, it may be necessary to introduce scaling factors and offset values to account for calibration and model bias associated with different metrologies.

In yet another further aspect, a model building and analysis engine performs principal component analysis (PCA) to transform one or more sets of parameter values into one or more sets of parameter values with reduced correlation PCA involves converting a set of possibly correlated parameters into a set of linearly uncorrelated parameters by linear coordinate transformation.

In yet another further aspect, the specimen under inspection includes field enhancement elements to increase parameter sensitivity to x-ray and optical metrology. Field enhancement elements are structures employed to enhance the measurement sensitivity associated with parameters of interest as well as to break parameter correlations.

In yet another further aspect, the structure of models of the response of the specimen to at least two different measurement technologies is altered based on the quality of the fit between the models and the corresponding measurement data. In some examples, the structure of the geometric model is altered based on the quality of the fit between the response models and the corresponding measurement data.

The foregoing is a summary and thus contains, by necessity, simplifications, generalizations and omissions of detail; consequently, those skilled in the art will appreciate that the summary is illustrative only and is not limiting in any way. Other aspects, inventive features, and advantages of the devices and/or processes described herein will become apparent in the non-limiting detailed description set forth herein.

DETAILED DESCRIPTION

Figure 1:
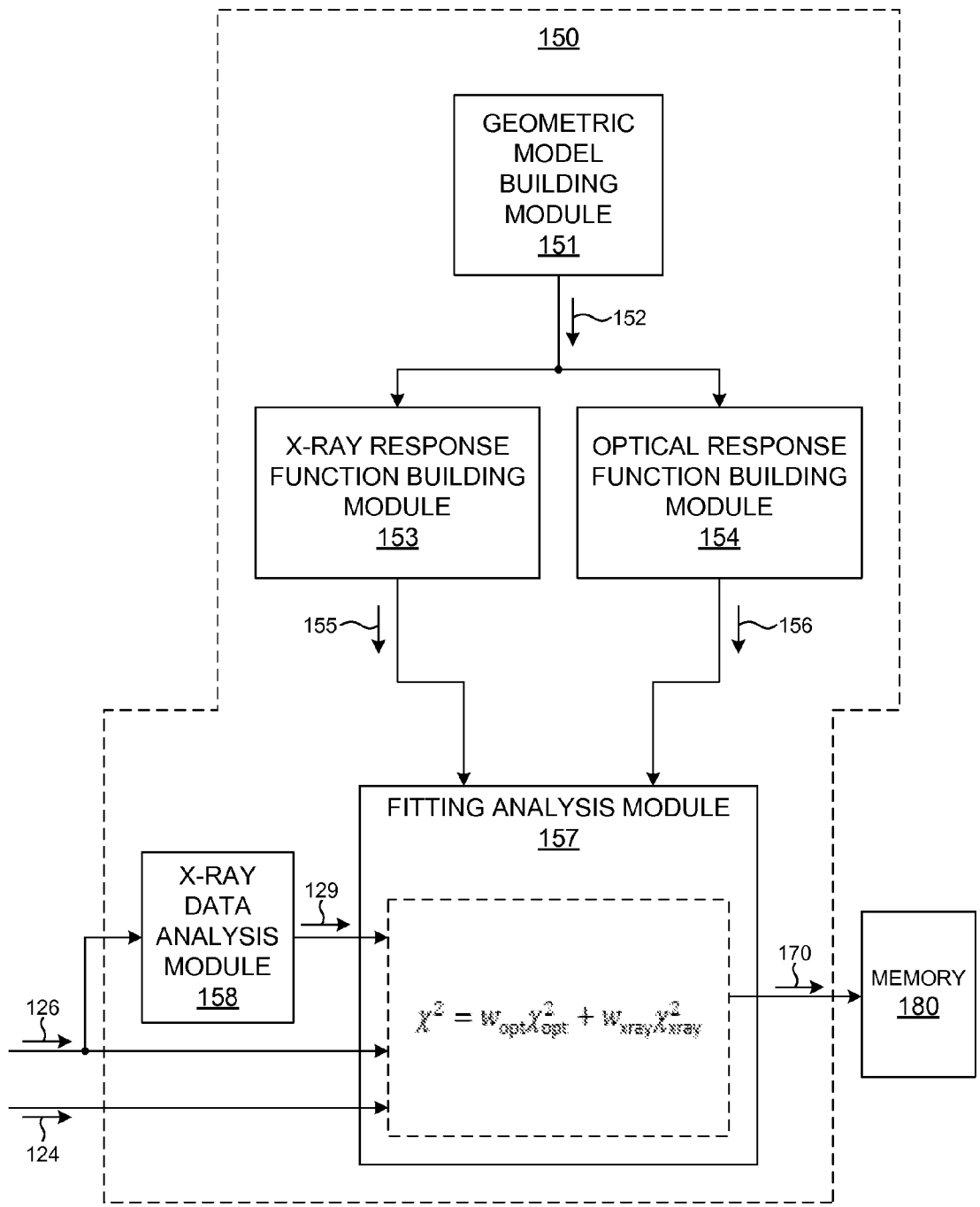
FIG. 1 is a diagram illustrative of an exemplary model building and analysis engine 150 configured to implement model building and analysis functionality as described herein.

Methods and systems for performing measurements of structural and material characteristics (e.g., material composition, dimensional characteristics of structures and films, etc.) associated with different semiconductor fabrication processes are presented. As described herein, one or more structural parameters of a semiconductor specimen are determined by fitting models of the response of the specimen to measurements collected by different measurement techniques in a combined analysis. Reference will now be made in detail to background examples and some embodiments of the invention, examples of which are illustrated in the accompanying drawings.

In one aspect, x-ray measurement data of a specimen is analyzed to determine at least one specimen parameter value that is treated as a constant in a combined analysis of both optical measurements and x-ray measurements of the specimen. For example, a particular structural property (e.g., layer thickness, structure volume, etc.), or a particular material property such as an elemental composition of the specimen is determined based on x-ray measurement data. The specimen parameter(s) determined from the x-ray measurement data are treated as constants in a combined analysis of both optical measurements and x-ray measurements of the specimen. This enables increased measurement sensitivity and throughput due to the complementary nature of x-ray and optical techniques. Measurement precision and accuracy can be improved by identifying shared model parameters that are mathematically resolved sequentially or in parallel using data sets derived from x-ray and optical measurements. Measuring shared parameters with a diversity of measurement technologies reduces correlations among parameters and improves measurement accuracy.

In one further aspect, the models of the response of the specimen to at least two different measurement technologies share at least one common geometric parameter. In another further aspect, the models of the response of the specimen to at least two different measurement technologies are based on the same geometric model.

In general, the combined x-ray and the optical measurement techniques discussed herein are indirect methods of measuring some physical properties of the specimen under inspection. However, some physical properties of the specimen can be directly determined with high precision based on x-ray measurement data. In some examples, the precise elemental composition of a structure of a specimen is determined directly from x-ray measurement data. This result is then used as a fixed parameter in a subsequent indirect analysis using x-ray and optical measurement data. In one non-limiting example, the elemental composition of a structure may be directly determined with high precision based on x-ray measurement data. Based on the known elemental composition, the complex index of refraction of the structure is precisely determined, and is treated as a constant in subsequent analysis.

In cases where the measured values cannot be used to directly determine the physical properties of the specimen. The nominal measurement process consists of parameterization of the structure (e.g., film thicknesses, critical dimensions, refraction indices, etc.) and the machine (e.g., wavelengths, angles of incidence, polarization angles, etc.). A model is created that attempts to predict the measured values. The model includes parameters associated with the machine ($P_{machine}$) and the specimen ($P_{specimen}$).

Machine parameters are parameters used to characterize the metrology tool itself. Exemplary machine parameters include angle of incidence (AOI), analyzer angle ($A_0$), polarizer angle ($P_0$), illumination wavelength, numerical aperture (NA), etc. Specimen parameters are parameters used to characterize the specimen. For a thin film specimen, exemplary specimen parameters include refractive index, dielectric function tensor, nominal layer thickness of all layers, layer sequence, etc. For measurement purposes, the machine parameters are treated as known, fixed parameters and the specimen parameters are treated as unknown, floating parameters. The floating parameters are resolved by a fitting process (e.g., regression, library matching, etc.) that produces the best fit between theoretical predictions and experimental data. The unknown specimen parameters, $P_{specimen}$, are varied and the model output values are calculated until a set of specimen parameter values are determined that results in a close match between the model output values and the experimentally measured values.

FIG. 1 is a diagram illustrative of an exemplary model building and analysis engine 150 configured to implement model building and analysis functionality as described herein. In one example, model building and analysis engine 150 is implemented by a computing system (e.g., computing system 130 illustrated in FIG. 2).

Model building and analysis engine 150 includes a geometric model building module 151 configured to generate a geometric model 152 of a measured structure of a specimen. Model building and analysis engine 150 also includes an x-ray response function building module 153 and an optical response building module 154 to generate an x-ray response model 155 and an optical response model 156, respectively. In some examples, each model includes at least one shared geometric parameter from the geometric model. Model building and analysis engine 150 also includes an x-ray data analysis module 158 to directly determine at least one specimen parameter value (e.g., layer thickness, structure volume, elemental composition, etc.) based on x-ray measurement data.

Model building and analysis engine 150 also includes a fitting analysis module 157 configured to resolve at least one specimen parameter value 170 by fitting the optical response model 156 with an amount of optical measurement data 124 and fitting the x-ray response model 155 with an amount of x-ray measurement data 126 in a combined analysis. The specimen parameter values determined by x-ray data analysis module 158 are treated as constants in the combined analysis of both optical measurements and x-ray measurements of the specimen.

Figure 3:
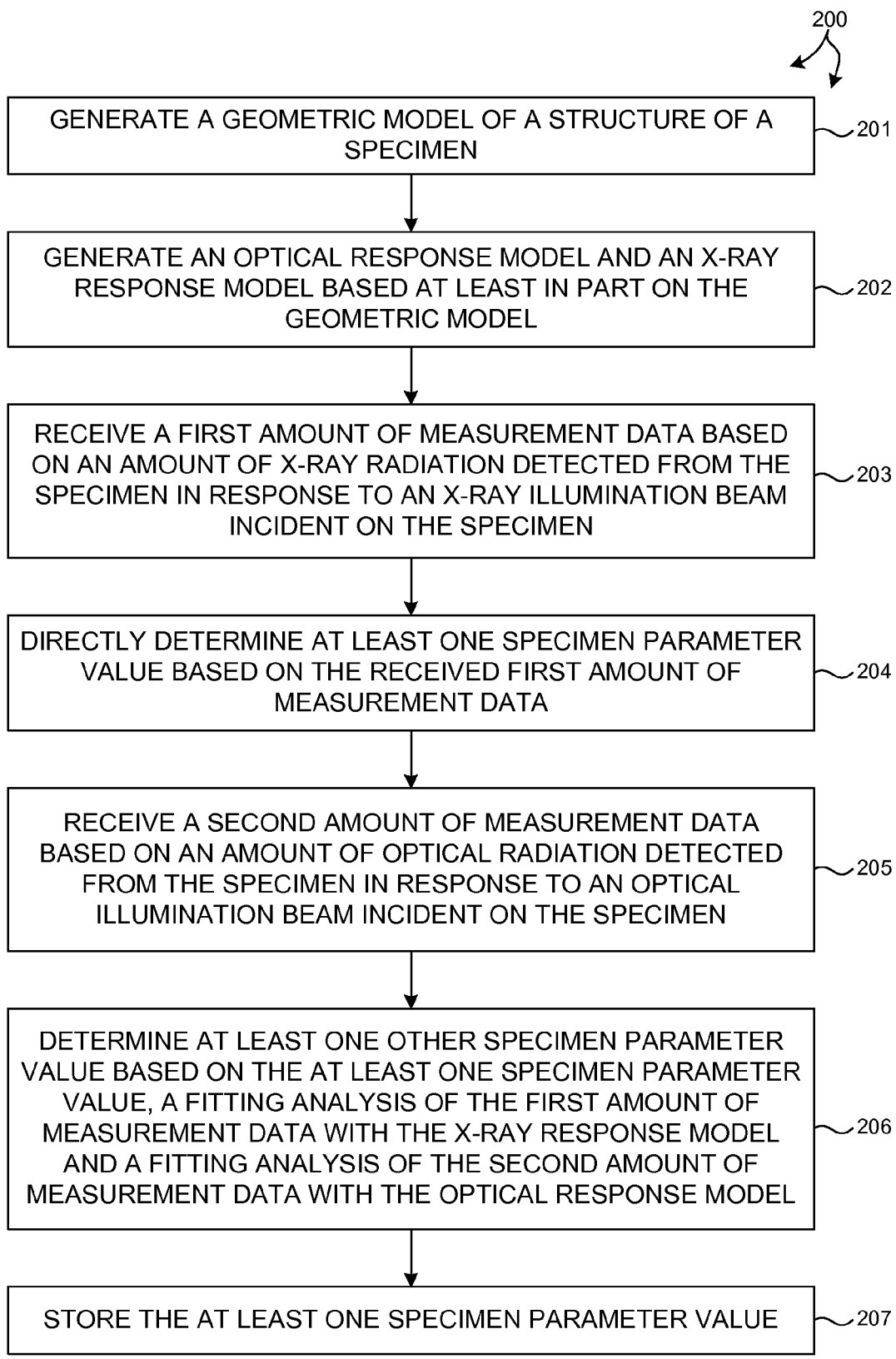
FIG. 3 is a flowchart illustrative of a method 200 suitable for implementation by the model building and analysis engine 150 of the present invention.

FIG. 3 illustrates a method 200 suitable for implementation by the model building and analysis engine 150 of the present invention. In one aspect, it is recognized that data processing blocks of method 200 may be carried out via a pre-programmed algorithm executed by one or more processors of computing system 130. While the following description of the model building and analysis engine 150 is presented in the context of combined metrology system 100, it is recognized herein that the particular structural aspects of combined metrology system 100 do not represent limitations and should be interpreted as illustrative only.

In block 201, geometric model building module 151 of model building and analysis engine 150 generates a geometric model 152 of at least one structure of a specimen. In some embodiments, geometric model 152 also includes material properties of the specimen.

In block 202, x-ray response function building module 153 generates an x-ray response model 155 based at least in part on the geometric model 152. Similarly, optical response function building module 154 generates an optical response model 156 based at least in part on the geometric model 152. In some embodiments, both the optical response model 155 and the x-ray response model 156 include at least one common geometric parameter from the geometric model 152.

As depicted in FIG. 1, the geometric model 152 is received as input to x-ray response function building module 153 and optical response function building module 154. X-ray response function building module 153 generates a x-ray response function model 155 based at least in part on the geometric model 152.

In some examples, the x-ray response function model 155 is based on a fundamental parameters model that relates the measured signal associated with each material element to the sum of contributions from all materials that include the element. In one example, an x-ray fluorescence (XRF) simulation is based on the intensity of fluoresced radiation for a specific element given by the following fundamental parameters model for a planar film.

$$I_x(s_n) = I_\gamma \frac{\tau\rho(s_n)_m \omega R}{\left(\frac{\mu_\gamma(s_n)}{\cos\phi} + \frac{\mu_x(s_n)}{\cos\theta}\right)} \left\{1 - \exp\left[-\left(\frac{\mu_\gamma(s_n)}{\cos\phi} + \frac{\mu_x(s_n)}{\cos\theta}\right)L\right]\right\} \frac{\Omega}{4\pi\cos\theta} \quad (1)$$

where $I_x$ is the x-ray rate at the detector surface at fluoresced energy x for element $s_n$, $I_y$ is the x-ray rate at the sample surface at excitation energy, $\gamma$, $\tau$, is the photoelectric cross section at excitation energy, $\gamma$, $\rho(s_n)_m$ is the concentration (density) of element $s_n$ in material m, $\omega$, is the K(L) fluorescence yield, R is the radiative rate for K(L), $\mu_\gamma$, is the linear attenuation coefficient at energy, $\gamma$, for a layer with element $s_n$, $\mu_x$, is the linear attenuation coefficient at energy, x, for the layer with element $s_n$, $\phi$, is the incident angle of the x-ray radiation, $\theta$, is the exiting angle of the x-ray radiation, L, is the layer thickness, and, $\Omega$, is the solid angle of the x-ray detector.

In the limit of relatively thin films, e.g., film having a thickness less than one hundred nanometers:

$$I_x(s_n) \approx I_\gamma \tau\rho(s_n)_m \omega RL \frac{\Omega}{4\pi\cos\theta} \quad (2)$$

where, $$\left(\frac{\mu_\gamma}{\cos\phi} + \frac{\mu_x}{\cos\theta}\right)L \ll 1 \quad (3)$$

For a periodic structure with cell area $A_{cell}$ and volume $V_{m,s}$, where, $V_{m,s}$, is the total volume of material m within the cell containing element $s_n$ at density $\rho_m$, the parameter, L, in equation (2) can substituted with the term, $V_m/A_{cell}$. If several materials within the structure contain element $s_n$:

$$I_x(s_n) \approx I_y \tau \omega R \frac{\Omega}{4\pi\cos\theta} \sum_m \rho(s_n)_m \frac{V_m}{A_{cell}} \quad (4)$$

Other types of X-ray measurements (e.g., XPS) can be modeled with appropriate known methods.

Similarly, optical response function building module 154 generates an optical response function model 156 based at least in part on the geometric model 152. In some examples, optical response function model 156 is based on rigorous coupled-wave analysis (RCWA) where Maxwell's equations are solved to predict the optical scattering from the specimen model.

In general, specimen parameters can be deterministic (e.g., film thicknesses, CD, SWA, etc.), statistical (e.g., rms height of sidewall roughness, roughness correlation length, etc.), or any combination of deterministic and statistical parameters as long as proper models describing x-ray and optical beam interaction with the specimen are used.

In block 203, x-ray measurement data associated with measurements of the specimen by an x-ray metrology system is received by x-ray data analysis module 158. The x-ray measurement data is based on an amount of x-ray radiation detected from the specimen in response to x-ray illumination incident on the specimen. As depicted in FIG. 1, x-ray data analysis module 158 receives x-ray measurement data 126 generated by x-ray detector 116 illustrated in FIG. 2.

In block 204, at least one specimen parameter value is directly determined based on the x-ray measurement data. X-ray data analysis module 158 receives x-ray measurement data 126 and directly determines structural and/or material parameter values. In one example, x-ray data analysis module 158 compares the modeled x-ray response (e.g., based on a fundamental parameters model) with the corresponding measured data to determine geometric as well as material parameters of the specimen. In one example, x-ray data analysis module 158 determines an elemental composition of the measured specimen, and thus the complex index of refraction associated with the specimen. The determined parameter(s) 129 are communicated to fitting analysis module 157.

In block 205, optical measurement data associated with measurements of the specimen by an optical metrology system is received by fitting analysis module 157. The optical measurement data is based on an amount of optical radiation detected from the specimen in response to optical illumination incident on the specimen. As depicted in FIG. 1, fitting analysis module 157 receives optical measurement data 124 generated by optical detector 123 illustrated in FIG. 2.

In block 206, at least one specimen parameter value 170 is determined based on specimen parameter(s) 129 determined by x-ray data analysis module 158, a fitting analysis of the x-ray measurement data 126 with the x-ray response model 155 and a fitting analysis of the optical measurement data 124 with the optical response model 156. Specimen parameter(s) 129, x-ray response function model 155, and optical response function model 156 are received as input to fitting analysis module 157. The fitting analysis module 157 compares the modeled x-ray and optical scattering with the corresponding measured data to determine geometric as well as material properties of the specimen. Specimen parameter(s) 129 are fixed in the combined analysis.

In some examples, the fitting of modeled data to experimental data is achieved by minimizing a chi-squared value. For example, for optical metrology, a chi-squared value can be defined as $$\chi^2_{opt} = \frac{1}{N_{opt}} \sum_i^{N_{opt}} \frac{\left(S_i^{opt.\,model}(u_1, \ldots, u_M) - S_i^{opt.\,experiment}\right)^2}{\sigma^2_{opt,i}} \quad (5)$$

where $S_i^{opt.\,experiment}$ is the measured optical signals 124 measured experimentally in the "channel" i, where the index i describes a set of system parameters such as wavelength, angular coordinate, polarization, etc. $S_i^{opt.\,model}(u_1, \ldots, u_M)$ is the modeled optical signal for the "channel" i, evaluated for a set of structure (target) parameters $u_1, \ldots, u_M$, where these parameters describe geometric (film thicknesses, CD, sidewall angle, overlay, etc.) and material (refractive indices, absorption coefficients, dispersion model parameters), etc. $\sigma_{opt,i}$ is the uncertainty associated with "channel" i. $N_{opt}$ is the total number of channels in the optical metrology. M is the number of parameters characterizing the metrology target. Exemplary methods and systems for model based analysis of optical spectroscopic measurement data is described in U.S. Pat. No. 7,478,019, issued on Jan. 13, 2009, to KLA-Tencor Corp., the entirety of which is incorporated herein by reference.

Similarly, for x-ray measurements (e.g. for XRF or XPS), a chi-squared value can be defined as $$\chi^2_{xray} = \frac{1}{N_{xray}} \sum_j^{N_{xray}} \frac{\left(S_j^{xray\,model}(v_1, \ldots, v_L) - S_j^{xray\,experiment}\right)^2}{\sigma^2_{xray,j}} \quad (6)$$

Where, $S_j^{xray\,experiment}$ is the measured x-ray signals 126 in the "channel" j, where the index j describes a set of system parameters such as energy, angular coordinate, etc. $S_j^{xray\,model}(v_1, \ldots, v_L)$ is the modeled x-ray signal $S_j$ for the "channel" j, evaluated for a set of structure (target) parameters $v_1, \ldots, v_L$, where these parameters describe geometric (film thicknesses, CD, sidewall angle, overlay, structure volume, etc.) and material (atomic density, elemental composition, etc.) properties. $\sigma_{xray,j}$ is the uncertainty associated with the jth channel. $N_{xray}$ is the total number of channels in the x-ray metrology. L is the number of parameters characterizing the metrology target.

In another example, the chi-squared value associated with x-ray measurements is defined as $$\chi^2_{xray} = \frac{1}{N_{material}} \sum_m^{N_{material}} \frac{\left(V_m^{model}(v_1, \ldots, v_L) - V_m^{xray\,experiment}\right)^2}{\sigma^2_{V\,xray,m}} \quad (7)$$

Where, $V_m^{xray\,experiment}$ is the volume of material m calculated from one or several measured x-ray signals using calibrated target response or fundamental parameter models, $V_m^{xray\,model}(v_1, \ldots, v_L)$ is the modeled volume Vm for material m, evaluated for a set of structure (target) parameters $v_1, \ldots, v_L$, where these parameters describe geometric (film thicknesses, CD, sidewall angle, etc.), $\sigma_{V\,xray,m}$ is the uncertainty associated with the volume of material m, $N_{material}$ is the total number of materials, and L is the number of parameters characterizing the metrology target.

Equations (5), (6), and (7) assume that the uncertainties associated with different channels are uncorrelated. In examples where the uncertainties associated with the different channels are correlated, a covariance between the uncertainties, can be calculated. In these examples a chi-squared value for optical measurements can be expressed as $$\chi_{opt}^2 = \frac{1}{N_{opt}} \left( \overline{S}_i^{opt.\,model}(u_1, \ldots, u_M) - \overline{S}_i^{opt.\,experiment} \right)^T \quad (8)$$

$$V_{opt}^{-1} \left( \overline{S}_i^{opt.\,model}(u_1, \ldots, u_M) - \overline{S}_i^{opt.\,experiment} \right)$$

where, $V_{opt}$ is the covariance matrix of the optical channel uncertainties, and T denotes the transpose. A chi-squared value for x-ray measurements can be calculated in the same manner.

The combined fitting of optical metrology data and x-ray metrology data capable of direct elemental identification or direct determination of material composition (e.g., XRF, XPS, etc.) is advantageous for any type of x-ray and optical technology that provides complementary sensitivity to geometric and/or material parameters of interest. This is specifically the case where at least one parameter is shared or linked between the x-ray and the optical models.

However, in some examples, the x-ray and optical models do not share a common parameter, and the combined analysis is enhanced by direct determination of elemental composition of the measurement target based on x-ray metrology.

In some examples, the elemental composition of a measurement target is determined based on x-ray measurement data 126 by x-ray data analysis module 158. Subsequently, fitting analysis module 157 calibrates the optical response to geometric variation using x-ray measurement data 126 collected from a series of metrology targets. For example, x-ray data analysis module 158 determines the total volume of specific material within the cell of a periodic structure based on x-ray measurement data 126. The total volume of specified material is expressed in terms of geometric model parameters, and possibly, a material optical dispersion model. In one example, fitting analysis module 157 solves at least one parameter in terms of other parameters and the total volume determined by x-ray data analysis module 158. Thus, the number of unknown parameters is reduced. In another example, fitting analysis module 157 minimizes a cost function that includes terms for both measured optical signal versus model optical signal and measured volume of material, or measured volumes of several materials.

In some other examples, fitting analysis module 157 determines the optical dispersion model parameters for optical analysis based on the elemental composition of a measurement target determined by x-ray data analysis module 158. Fitting analysis module 157 calibrates the optical response to compositional variation using the optical 124 and x-ray data 126 from a series of selected metrology targets. In some examples, the optical dispersion model parameters are calculated from an analysis of component dispersion models and a fundamental physical model such as a Bruggeman effective medium model. In some other examples, the optical dispersion model parameters are determined from a look-up table that expresses optical dispersion as a function of chemical composition.

The set of target parameters for the optical model (i.e., $\{u_1, \ldots, u_M\}$) and the x-ray model (i.e., $\{v_1, \ldots, v_L\}$) are not the same in general. Differences in material constants and functions needed to describe optical and x-ray interaction processes give rise to different target parameters. In addition, the targets described by the optical model and the x-ray model may be the same or different. For example, separate, multiple film and periodic structure targets may be used to determine the film and periodic structure parameters of a common structure. In another example, simultaneous x-ray and optical analyses of a large area target may be performed along with x-ray analysis of a small area target. The parameters of the large area target are correlated to the x-ray measurements and the correlation is applied to determine corresponding parameters of the small area target.

In yet another further aspect, model building and analysis engine 150 performs x-ray and optical analyses using common or multiple targets wherein at least one common parameter is coupled during the analysis. In some examples, at least one parameter is common between the x-ray response function model 155 and the optical response function model 156. The common parameter is either identical or related to each other by an unambiguous algebraic transformation. In some examples, target parameters such as film thicknesses, CD, overlay, etc. are common between both the x-ray response function model 155 and the optical response function model 156.

In one further aspect, the fitting of the optical response model with an amount of optical measurement data and the fitting of the x-ray response model with an amount of x-ray measurement data can be done sequentially, in parallel, or by a combination of sequential and parallel analyses. In some examples, model building and analysis engine 150 improves the accuracy of measured parameters by any combination of feed sideways analysis, feed forward analysis, and parallel analysis. Feed sideways analysis refers to taking multiple data sets on different areas of the same specimen and passing common parameters determined from one dataset onto a subsequent dataset for analysis. Feed forward analysis refers to taking data sets on different specimens and passing common parameters forward to subsequent analyses using a stepwise copy exact parameter feed forward approach. Parallel analysis refers to the parallel or concurrent application of a non-linear fitting methodology to multiple datasets where at least one common parameter is coupled during the fitting.

In some other examples, fitting analysis module 157 resolves at least one specimen parameter value by performing a parallel fitting analysis of x-ray response model 155 with x-ray measurement data 126 and optical response model 156 with optical measurement data 124. By way of a non-limiting example, a chi-squared function suitable for parallel analysis can be defined as $$\chi^2 = w_{opt} \chi_{opt}^2 + w_{xray} \chi_{xray}^2 \quad (9)$$

where $w_{opt}$ and $w_{xray}$ are weighting coefficients that are assigned to the optical and x-ray metrologies. In the simplest case, $w_{opt} = w_{xray} = 1$. However, assigning different weights often enhances the more relevant metrology. The selection of proper weights is usually done by analysis of experimental data versus reference metrology and/or measuring pre-programmed design of experiments (DOE) parameter variations on special DOE targets.

In some examples, model building and analysis engine 150 improves the accuracy of measured parameters by performing multiple tool and structure analysis. Multiple tool and structure analysis refers to a feed forward, feed sideways, or parallel analysis based on regression, a look-up table (i.e., "library" matching), or another fitting procedure of multiple datasets. Exemplary methods and systems for multiple tool and structure analysis is described in U.S. Pat. No. 7,478,019, issued on Jan. 13, 2009, to KLA-Tencor Corp., the entirety of which is incorporated herein by reference.

In some examples, fitting analysis module 157 resolves at least one specimen parameter value by sequentially performing a fitting analysis of the x-ray response model 155 with x-ray measurement data 126 and a fitting analysis of the optical response model 156 with optical measurement data 124. In some examples, $\chi_{opt}^2$ is optimized first, and any resolved, common specimen parameter values are treated as constants in the subsequent optimization of $\chi_{xray}^2$. Similarly, in some other examples, $\chi_{xray}^2$ is optimized first, and any resolved, common specimen parameter values are treated as constants in the subsequent optimization of $\chi_{opt}^2$.

Optical and x-ray metrologies may contain more than one respective technology when calculating chi-squared values. For example, $\chi_{xray}^2$ may be calculated for the combined use of grazing incidence XRF and XPS with a weight coefficient given to each technology. Likewise, $\chi_{opt}^2$ may be calculated for the combined use of spectroscopic ellipsometry, beam profile reflectometry and spectroscopic reflectometry with a weight coefficient assigned to each technology.

In another further aspect, the number of floating target parameters of the optical model, $\{u_1, \ldots, u_M\}$, and the number of floating target parameters of the x-ray model, $\{v_1, \ldots, v_L\}$ are reduced by linking some of the parameters. In some examples, common geometric parameters are treated as a single parameter. By way of example, if u1 and v1 both represent the thickness of a particular film, the values of u1 and v1 are constrained to be the same value.

In some other examples, it may be necessary to introduce scaling factors and offset values to account for calibration and model bias of optical and x-ray metrologies. By way of example, if u1 and v1 both represent the thickness of a particular film, the value of u1 is constrained to be a function of v1 (e.g., u1=f1*v1+d1, wherein f1 and d1 are constants). Scaling factors (e.g., f1) and offset values (e.g., d1) are not floating parameters and are determined before the global optimization is performed. Calibration of scaling factors and offset values may be performed with the aid of transmission electron microscopy (TEM), atomic force microscopy (AFM), or other methods. Moreover, more complex ways to link structure parameters are also possible.

As described hereinbefore, the fitting of x-ray and optical models with measurement data is achieved by the least squares minimization of chi-squared values. However, in general, the fitting of x-ray and optical data may be achieved by other functions. This may be advantageous, for example, in cases when outliers are present. Exemplary functions are presented by P. J. Huber in "Robust Statistics," John Wiley and Sons (2004), the subject matter of which is incorporated herein by reference.

In block 207, at least one specimen parameter value determined in block 206 is stored. As illustrated in FIG. 1, fitting analysis module 157 communicates specimen parameter value 170 to memory 180 for storage in memory 180.

In a further aspect, model building and analysis engine 150 performs principal component analysis (PCA) to transform one or more sets of parameter values (e.g., $\{u_1, \ldots, u_M\}$ and $\{v_1, \ldots, v_L\}$) into one or more sets of parameter values with reduced correlation (e.g., $\{u'_1, \ldots, u'_M\}$ and $\{v'_1, \ldots, v'_L\}$). PCA involves converting a set of possibly correlated parameters into a set of linearly uncorrelated parameters by linear coordinate transformation.

In another further aspect, the specimen under inspection includes field enhancement elements to increase parameter sensitivity to x-ray and optical metrology. Field enhancement elements are structures employed to enhance the measurement sensitivity associated with parameters of interest as well as to break parameter correlations.

In yet another further aspect, the structure of the models of the response of the specimen to at least two different measurement technologies are altered based on the quality of the fit between the models and the corresponding measurement data. In some examples, the structure of the geometric model is altered based on the quality of the fit between the response models and the corresponding measurement data.

Figure 4:
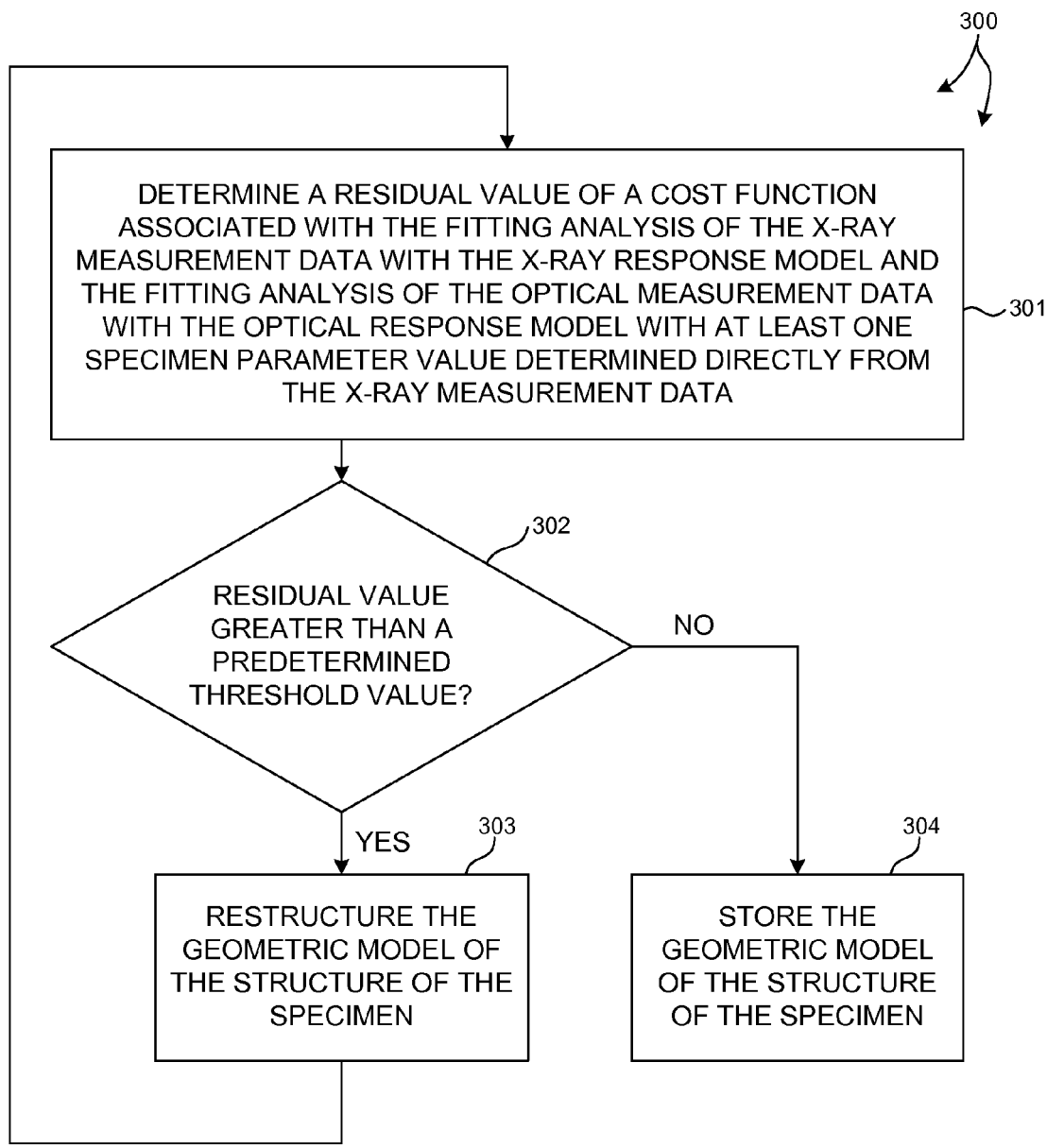
FIG. 4 is flowchart illustrative of a method 300 suitable for implementation by the model building and analysis engine 150 of the present invention.

FIG. 4 illustrates a method 300 suitable for implementation by the model building and analysis engine 150 of the present invention. In one aspect, it is recognized that data processing blocks of method 300 may be carried out via a pre-programmed algorithm executed by one or more processors of computing system 130. While the following description of the model building and analysis engine 150 is presented in the context of combined metrology system 100, it is recognized herein that the particular structural aspects of combined metrology system 100 do not represent limitations and should be interpreted as illustrative only.

In block 301, fitting analysis module 157 determines a residual value of a cost function associated with the fitting analysis of block 206 of method 200. In one example, fitting analysis module 157 determines the residual value of a cost function based on the magnitude of the optimization cost function (or functions) after the iterative optimization has been completed.

In block 302, fitting analysis module 157 determines whether the residual value exceeds a predetermined threshold value. In this manner, fitting analysis module 157 evaluates the quality of the fit between the x-ray and optical response models and the corresponding measurement data.

In block 303, the geometric model is restructured if the residual value exceeds the predetermined threshold value. For example if the value of $\chi^2$ exceeds a predetermined threshold value, model building and analysis engine 150 determines that the fit quality is low and the underlying measurement models need to be restructured to improve measurement results. In this manner, the quality of the data fit is used to check the validity of the parametric models used to describe the structure. In one example, model building and analysis engine 150 restructures the geometric model by calculating the Jacobian matrix associated with the geometric model parameters and then restructures the model by transforming the model parameters to minimize the largest value of the Jacobian matrix. The aforementioned approach is provided by way of non-limiting example. Many other approaches to model restructuring may be contemplated.

For example, in some measurement scenarios, the target structure is a periodic grating parameterized in each period by a profile, film thicknesses, and material properties. An adequate fit may be achieved based on fitting an optical model with optical data alone. However, simultaneously fitting optical and x-ray models to optical and x-ray measurement data including the elemental composition of the measurement target directly determined based on x-ray measurement data reveals an unacceptably poor fit (i.e., the residual value of the optimization cost function is too high). In response, the structural model can be altered until a good fit is determined. Note that altering the model involves changing the parameterization of the target structure (e.g., adding or changing features such as footers, line edge roughness, refining dielectric properties, etc.). In this manner the optimization results provided by the model building and analysis engine 150 can be used to improve the structural model until it is sufficiently accurate.

In another example, in some measurement scenarios, an adequate fit of an optical model with optical data is achieved by adjusting model parameters and machine parameters (e.g., wavelength, tilt angle, noise, etc.). While this may work well within a small process window, it is often found that metrology systems operating in this manner are not capable of tracking practical process variations. Adding an x-ray based metrology capability (e.g., XPS, XRF, etc.) to directly determine elemental composition, in addition to the optically based metrology often reveals the deficiency of the model. In this scenario, model building and analysis engine 150 is used to identify the model deficiencies and alter the parameterization of the structure model. For example, a simple trapezoid model may be completely adequate to fit spectroscopic ellipsometry (SE) data. However, additional parameters such as composition, elemental identification, film thickness and shape inferred volumetrically may be directly measured using x-ray metrology techniques such as XRF, XPS, etc. This, in turn, improves the capability of the optical measurement system due to the use of a correct structure model.

In some examples, a combined fitting analysis including both optical and x-ray measurement data is used to develop an optimized structural model, and then only one of the measurement technologies (e.g., a higher throughput optical metrology technology) is used for production measurements.

In block 304, the geometric model is stored if the residual value does not exceed the predetermined threshold value.

As illustrated in FIG. 4, blocks 301-303 may be performed iteratively until a satisfactory result is achieved (i.e., the residual value does not exceed the predetermined threshold value) at which point the model is stored for further use.

Figure 2:
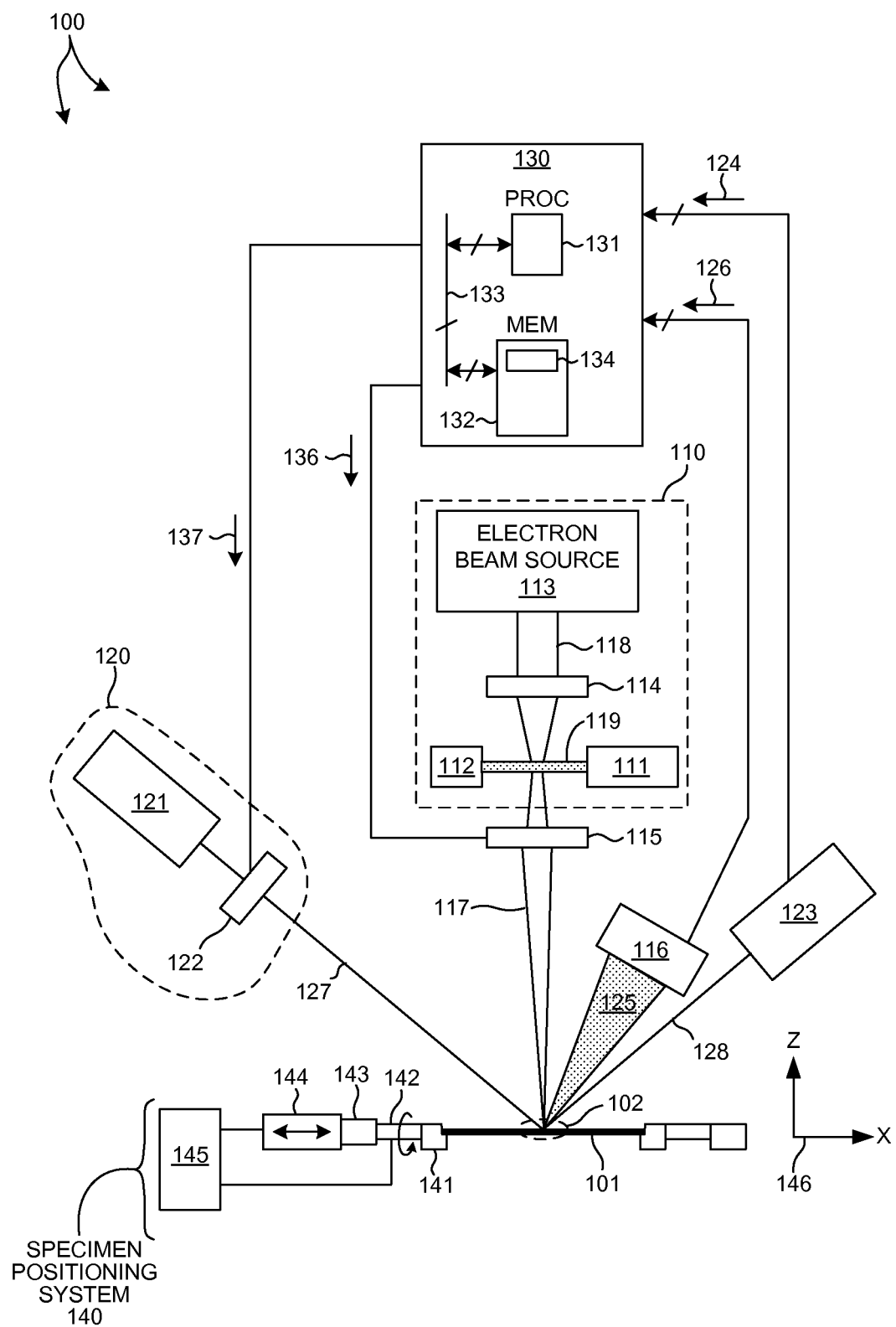
FIG. 2 is a diagram illustrative of a combined metrology tool 100 for measuring characteristics of a specimen with two different measurement techniques. Combined metrology tool 100 includes computing system 130 configured as a model building and analysis engine configured to implement model building and analysis functionality as described herein.

FIG. 2 illustrates a combined metrology tool 100 for measuring characteristics of a specimen with two different measurement techniques. In the embodiment depicted in FIG. 2, computing system 130 is configured as a model building and analysis engine configured to implement model building and analysis functionality as described herein. As shown in FIG. 2, the system 100 may be used to perform combined optical scatterometry measurements and x-ray measurements over an inspection area 102 of a specimen 101 disposed on a specimen positioning system 140. In some embodiments, the inspection area 102 has a spot size of fifty micrometers or less. In some embodiments, system 100 is configured to perform x-ray fluorescence (XRF) measurements. In some other embodiments, system 100 is configured to perform x-ray photoelectron spectroscopy (XPS).

In general, and as depicted in FIG. 2, metrology tool 100 includes an x-ray illumination source 110, x-ray beam shaping optics 115, and an x-ray detector 116. X-ray illumination source 110 produces an x-ray beam 117 incident on inspection area 102 of specimen 101. In some embodiments, the x-ray illumination source 110 is configured to generate wavelengths between 0.01 nanometers and 1 nanometer. X-ray optics 115 shape and direct incident x-ray beam 117 to specimen 101. In some examples, x-ray optics 115 monochromatize the x-ray beam that is incident on the specimen 101. In some examples, x-ray optics 115 collimate or focus the x-ray beam 117 onto inspection area 102 of specimen 101. In some embodiments, x-ray optics 115 includes one or more x-ray collimating mirrors, x-ray apertures, x-ray monochromators, and x-ray beam stops, multi-layer optics, refractive optics, diffractive optics such as zone plates, or any combination thereof.

In the embodiment depicted in FIG. 2, x-ray illumination source 110 is a high brightness, liquid metal jet x-ray illumination source. A jet of liquid metal 119 is produced from a liquid metal container 111 and collected in a liquid metal collector 112. A liquid metal circulation system (not shown) returns liquid metal collected by collector 112 to liquid metal container 111. The jet of liquid metal 119 includes one or more elements. By way of non-limiting example, the jet of liquid metal 119 includes any of Aluminum, Gallium, Indium, Tin, Thallium, and Bismuth. In this manner, the jet of liquid metal 119 produces x-ray lines corresponding with its constituent elements. An electron beam source 113 (e.g., electron gun) produces a stream of electrons 118 that is directed by electron optics 114 to the jet of liquid metal 119. Suitable electron optics 114 includes electromagnets, permanent magnets, or a combination of electromagnets and permanent magnets for focusing the electron beam and directing the beam at the liquid metal jet. The coincidence of the jet of liquid metal 119 and the stream of electrons 118 produces an x-ray beam 117 incident on inspection area 102 of specimen 101. Exemplary methods and systems for generating high brightness, liquid metal x-ray illumination are described in U.S. Pat. No. 7,929,667, issued on Apr. 19, 2011, to KLA-Tencor Corp., the entirety of which is incorporated herein by reference.

In the embodiment depicted in FIG. 2, x-ray illumination source 110 is a liquid metal jet x-ray illumination source. However, in general, any x-ray illumination source may be contemplated within the scope of this patent document.

X-ray detector 116 collects x-ray radiation 125 from specimen 101 and generates an output signal 126 indicative of properties of specimen 101 that are sensitive to the incident x-ray radiation. X-rays 125 are collected by x-ray detector 116 while specimen positioning system 140 locates and orients specimen 101. The x-ray detector 116 is able to resolve one or more x-ray photon energies and produces signals for each x-ray energy component indicative of properties of the specimen. In some embodiments, the x-ray detector 116 includes any of a CCD array, a microchannel plate, a photodiode array, a microstrip proportional counter, a gas filled proportional counter, and a scintillator. In some embodiments, x-ray detector 116 is a wavelength dispersive x-ray detector, for example, in embodiments of system 100 implementing wavelength dispersive x-ray fluorescence (WD-XRF) metrology. In some other embodiments, x-ray detector 116 is an energy dispersive x-ray detector, for example, in embodiments of system 100 implementing energy dispersive x-ray fluorescence (ED-XRF) metrology.

Combined metrology tool 100 also includes an optical illumination system 120 and an optical detector 123. Optical illumination system 120 includes an optical illumination source 121 and optical illumination optics 122 configured to shape and direct incident optical illumination beam 127 from optical illumination source 121 to the inspection area 102 of specimen 101. In some examples, the incident optical illumination beam 127 and the incident x-ray illumination beam 117 spatially overlap at the inspection area 102 of the specimen 101.

By way of non-limiting example, optical illumination source 121 includes one or more arc lamps, lasers, light emitting diodes, laser driven plasma sources, and laser driven supercontinuum sources, or any combination thereof. In general, any suitable optical illumination source may be contemplated. In some embodiments, optical illumination source 121 is configured to generate illumination light having wavelength components between 120 nanometers and 2000 nanometers.

Illumination optics 122 is configured to collimate or focus incident optical illumination beam 127 to inspection area 102 of specimen 101. In some examples, illumination optics 122 is configured to monochromatize incident optical illumination beam 127. In some embodiments, illumination optics 122 includes one or more optical mirrors, focusing or defocusing optics, optical waveplates, optical apertures, optical monochromators, and optical beam stops, or any combination thereof.

Optical detector 123 collects optical radiation 128 scattered from specimen 101 and generates an output signal 124 indicative of properties of specimen 101 that are sensitive to the incident optical radiation. Scattered optical radiation 128 is collected by optical detector 123 while specimen positioning system 140 locates and orients specimen 101 to produce angularly resolved scattered optical radiation. The optical detector 123 is able to resolve one or more optical photon energies and produces signals for each optical energy component indicative of properties of the specimen. In some embodiments, the optical detector 123 is any of a CCD array, a photodiode array, a CMOS detector and a photomultiplier tube.

Combined metrology tool 100 also includes a computing system 130 employed to acquire signals 124 and 126 generated by optical detector 123 and x-ray detector 116, respectively, and determine properties of the specimen based at least in part on the acquired signals. As illustrated in FIG. 2, computing system 130 is communicatively coupled to optical detector 123 and x-ray detector 116. In one aspect, computing system 130 receives measurement data 124 and 126 associated with simultaneous, critical dimension measurements of specimen 101 over an inspection area 102 illuminated by both an x-ray beam 117 and an optical illumination beam 127.

In one example, optical detector 123 is an optical spectrometer and measurement data 124 includes an indication of the measured spectral response of the specimen based on one or more sampling processes implemented by the optical spectrometer. Similarly, in one example, x-ray detector 116 is an x-ray spectrometer and measurement data 126 includes an indication of the measured spectral response of the specimen based on one or more sampling processes implemented by the x-ray spectrometer.

In a further embodiment, computing system 130 is configured to access model parameters in real-time, employing Real Time Critical Dimensioning (RTCD), or it may access libraries of pre-computed models for determining a value of at least one specimen parameter value associated with the specimen 101. In general, some form of CD-engine may be used to evaluate the difference between assigned CD parameters of a specimen and CD parameters associated with the measured specimen. Exemplary methods and systems for computing specimen parameter values are described in U.S. Pat. No. 7,826,071, issued on Nov. 2, 2010, to KLA-Tencor Corp., the entirety of which is incorporated herein by reference.

In one further aspect, combined metrology tool 100 includes a computing system (e.g., computing system 130) configured to implement beam control functionality as described herein. In the embodiment depicted in FIG. 2, computing system 130 is configured as a beam controller operable to control the positioning and spot size of the incident x-ray beam 117 and the incident optical illumination beam 127 such that they spatially overlap at the desired inspection area 102 of the specimen 101 at any point in time.

As illustrated in FIG. 2, computing system 130 is communicatively coupled to x-ray detector 116 and optical detector 123. Computing system 130 is configured to receive measurement data 124 from optical detector 123 and measurement data 126 from x-ray detector 116. In one example, measurement data 124 includes an indication of the measured optical response of the specimen. Based on the distribution of the measured optical response on the surface of detector 123, the location and area of incidence of optical illumination beam 127 on specimen 101 is determined by beam controller 130. In one example, pattern recognition techniques are applied by computing system 130 to determine the location and area of incidence of optical illumination beam 127 on specimen 101 based on measurement data 124. Similarly, measurement data 126 includes an indication of the measured x-ray response of the specimen. Based on the distribution of the measured x-ray response on the surface of detector 116, the location and area of incidence x-ray beam 117 on specimen 101 is determined by beam controller 130. In one example, pattern recognition techniques are applied by computing system 130 to determine the location and area of incidence of x-ray beam 117 on specimen 101 based on measurement data 124. In response computing system 130 generates a command signal 137 communicated to illumination optics 122 to redirect and reshape incident optical illumination beam 127 such that incident optical illumination beam 127 spatially overlaps incident x-ray beam 117 at the desired inspection area 102 of specimen 101. Similarly, beam controller 130 generates a command signal 136 communicated to any of electron optics 114 and x-ray optics 115 to redirect and reshape incident x-ray beam 117 such that incident x-ray beam 117 spatially overlaps incident optical illumination beam 127 at the desired inspection area 102 of specimen 101.

In another aspect, simultaneous x-ray measurements and optical scatterometry measurements of a particular inspection area are performed at a number of different out of plane orientations. This increases the precision and accuracy of measured parameters and reduces correlations among parameters by extending the number and diversity of data sets available for analysis to include a variety of large-angle, out of plane orientations. Measuring specimen parameters with a deeper, more diverse data set also reduces correlations among parameters and improves measurement accuracy.

As illustrated in FIG. 2, combined metrology tool 100 includes a specimen positioning system 140 configured to both align specimen 101 and orient specimen 101 with respect the optical scatterometer and the x-ray metrology system. Computing system 130 communicates command signals to motion controller 145 of specimen positioning system 140 that indicate the desired position of specimen 101. In response, motion controller 145 generates command signals to the various actuators of specimen positioning system 140 to achieve the desired positioning of specimen 101.

By way of non-limiting example, as illustrated in FIG. 2, specimen positioning system 140 includes an edge grip chuck 141 to fixedly attach specimen 101 to specimen positioning system 140. A rotational actuator 142 is configured to rotate edge grip chuck 141 and the attached specimen 101 with respect to a perimeter frame 143. In the depicted embodiment, rotational actuator 142 is configured to rotate specimen 101 about the x-axis of the coordinate system 146 illustrated in FIG. 2. As depicted in FIG. 2, a rotation of specimen 101 about the z-axis is an in plane rotation of specimen 101. Rotations about the x-axis and the y-axis (not shown) are out of plane rotations of specimen 101 that effectively tilt the surface of the specimen with respect to the metrology elements of metrology system 100. Although it is not illustrated, a second rotational actuator is configured to rotate specimen 101 about the y-axis. A linear actuator 144 is configured to translate perimeter frame 143 in the x-direction. Another linear actuator (not shown) is configured to translate perimeter frame 143 in the y-direction. In this manner, every location on the surface of specimen 101 is available for measurement over a range of out of plane angular positions.

In some embodiments, a location of specimen 101 is measured over several angular increments within a range of −45 degrees to +45 degrees with respect to the normal orientation of specimen 101. In other words, specimen positioning system 140 is configured to rotate specimen 101 over a large angular range about one or more axes of rotation aligned in-plane with the surface of specimen 101. In some embodiments, specimen positioning system 140 is configured to rotate specimen 101 within a range of at least 90 degrees about one or more axes of rotation aligned in-plane with the surface of specimen 101. In some embodiments, specimen positioning system is configured to rotate specimen 101 within a range of at least 60 degrees about one or more axes of rotation aligned in-plane with the surface of specimen 101. In some other embodiments, specimen positioning system is configured to rotate specimen 101 within a range of at least one degree about one or more axes of rotation aligned in-plane with the surface of specimen 101. In this manner, angle resolved measurements of specimen 101 are collected by metrology system 100 over any number of locations on the surface of specimen 101.

Typical optical scatterometry systems do not employ a specimen positioning system capable of orienting a specimen over a large range of out of plane angular positions (e.g., greater than +/− one degree). As a result, measurement information collected by these systems often lacks sensitivity to certain parameters or is unable to reduce correlations between parameters. However, the large, out of plane, angular positioning capability of specimen positioning system 140 expands measurement sensitivity and reduces correlations between parameters. For example, in a normal orientation, XRF is able to resolve the critical dimension of a feature (e.g., film thickness), but is largely insensitive to sidewall angle and height of a feature. However, by collecting measurement data over a broad range of out of plane angular positions, the sidewall angle and height of a feature can be resolved, for example, by a confocal XRF system. A confocal XRF system includes a polycapillary lens to focus the x-ray illumination beam onto the sample. X-ray radiation emanating from the confocal point is collected by a polycapillary half lens. In this manner, an XRF intensity signal is obtained over a small three dimensional region, enabling three dimensional elemental mapping of the sample. Three dimensional confocal XRF techniques are described in greater detail by W. M. Gibson and M. A. Kumakhow in "Applications of x-ray and neutron capillary optics," Proc. SPIE, 1736, pp. 172-189, 1992, the entirety of which is incorporated herein by reference.

It should be recognized that the various steps described throughout the present disclosure may be carried out by a single computer system 130 or, alternatively, a multiple computer system 130. Moreover, different subsystems of the system 100, such as the specimen positioning system 140, may include a computer system suitable for carrying out at least a portion of the steps described herein. Therefore, the aforementioned description should not be interpreted as a limitation on the present invention but merely an illustration. Further, the one or more computing systems 130 may be configured to perform any other step(s) of any of the method embodiments described herein.

In addition, the computer system 130 may be communicatively coupled to the optical detector 123, the x-ray detector 116, the optical illumination optics 122, and the x-ray illumination optics 115 in any manner known in the art. For example, the one or more computing systems 130 may be coupled to computing systems associated with the optical detector 123, the x-ray detector 116, the optical illumination optics 122, and the x-ray illumination optics 115, respectively. In another example, any of the optical detector 123, the x-ray detector 116, the optical illumination optics 122, and the x-ray illumination optics 115 may be controlled directly by a single computer system coupled to computer system 130.

The computer system 130 of the combined metrology system 100 may be configured to receive and/or acquire data or information from the subsystems of the system (e.g., optical detector 123, the x-ray detector 116, the optical illumination optics 122, and the x-ray illumination optics 115, and the like) by a transmission medium that may include wireline and/or wireless portions. In this manner, the transmission medium may serve as a data link between the computer system 130 and other subsystems of the system 100.

Computer system 130 of the combined metrology system 100 may be configured to receive and/or acquire data or information (e.g., measurement results, modeling inputs, modeling results, etc.) from other systems by a transmission medium that may include wireline and/or wireless portions. In this manner, the transmission medium may serve as a data link between the computer system 130 and other systems (e.g., memory on-board metrology system 100, external memory, or external systems). For example, the computing system 130 may be configured to receive measurement data (e.g., signals 124 and 126) from a storage medium (i.e., memory 132 or memory 180) via a data link. For instance, spectral results obtained using a spectrometer of any of x-ray detector 116 and optical detector 123 may be stored in a permanent or semi-permanent memory device (e.g., memory 132 or 180). In this regard, the spectral results may be imported from on-board memory or from an external memory system. Moreover, the computer system 116 may send data to other systems via a transmission medium. For instance, specimen parameter values 170 determined by computer system 130 may be stored in a permanent or semi-permanent memory device (e.g., memory 180). In this regard, measurement results may be exported to another system.

Computing system 130 may include, but is not limited to, a personal computer system, mainframe computer system, workstation, image computer, parallel processor, or any other device known in the art. In general, the term "computing system" may be broadly defined to encompass any device having one or more processors, which execute instructions from a memory medium.

Program instructions 134 implementing methods such as those described herein may be transmitted over a transmission medium such as a wire, cable, or wireless transmission link. For example, as illustrated in FIG. 2, program instructions stored in memory 132 are transmitted to processor 131 over bus 133. Program instructions 134 are stored in a computer readable medium (e.g., memory 132). Exemplary computer-readable media include read-only memory, a random access memory, a magnetic or optical disk, or a magnetic tape.

As described with reference to FIG. 2, combined metrology system includes an x-ray system and an optical scatterometer system. However, in general, combined analysis based on a combination of different optical metrology techniques and different x-ray based metrology techniques may be contemplated within the scope of this patent document.

Furthermore, measurements based on any optical and x-ray metrology technique participating in a combined analysis as described herein may be performed on one or more individual metrology tools, one or more combined metrology tools, or any combination thereof without limitation.

By way of non-limiting example, any of the following optical metrology techniques including, spectroscopic ellipsometry (including Mueller matrix ellipsometry), Mueller matrix spectroscopic ellipsometry, spectroscopic reflectometry, spectroscopic scatterometry, scatterometry overlay, beam profile reflectometry, (angle and polarization resolved), beam profile ellipsometry, single or multiple discrete wavelength ellipsometry, multiple angle of incidence ellipsometry, and spectroscopic polarimetry may be combined for analysis as described herein with any of the following x-ray metrology techniques including, but not limited to, x-ray photoelectron spectroscopy (XPS), x-ray fluorescence (XRF), confocal XRF, energy dispersive XRF (EDXRF), wavelength dispersive XRF (WDXRF), and grazing incidence x-ray fluorescence (GIXRF) within the scope of this patent document.

X-ray and optical metrology techniques applied in combination as described herein may be used to determine characteristics of semiconductor structures. Exemplary structures include, but are not limited to, FinFETs, low-dimensional structures such as nanowires or graphene, sub 10 nm structures, thin films, lithographic structures, through silicon vias (TSVs), memory structures such as DRAM, DRAM 4F2, FLASH and high aspect ratio memory structures. Exemplary structural characteristics include, but are not limited to, geometric parameters such as line edge roughness, line width roughness, pore size, pore density, side wall angle, profile, film thickness, critical dimension, pitch, and material parameters such as electron density, crystalline grain structure, morphology, orientation, stress, strain, elemental identification, and material composition.

By way of non-limiting example, XRF is used to determine the volume of outer and inner electrode structures and Transition Metal Oxide structures in ReRAM (memory) device structures (e.g., pillars). The directly determined volumes are fed forward into the optical measurement model to determine structure parameters.

In another non-limiting example, XRF is used to determine the effective thickness of pure metal film layers in a STT-MRAM (memory) film stack. The directly determined film thicknesses are fed forward to the optical measurement model to determine the thicknesses of metal oxide and metal alloy layers such as a CoFeB layer.

In yet another example, XRF or XPS is used to determine the elemental composition and film thickness of HfO2 layers, very thick films, and films in which the electron density is very similar to neighboring films. These thicknesses and elemental composition are fed forward to break parameter correlations in optical measurements.

In yet another example, XRF is used to measure the Germanium dose in advanced structures such as FinFETs. In these examples, the SiGe layer is stretched, so the Germanium dose is not uniform. The Germanium dose is determined based on the XRF measurements, and the results are used to determine the Germanium concentration in combination with volume measurements made using optical technologies.

In yet another example, XRF is use to measure the elemental composition of III-V materials. These parameters are fed forward to an analysis of optically based measurements of thickness and critical dimension, for example, by spectroscopic ellipsometry.

Figure 5:
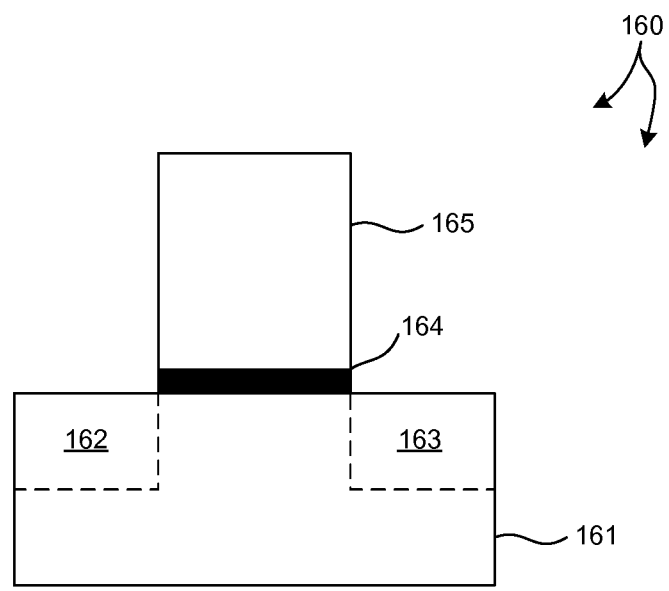
FIG. 5 is a diagram illustrative of a high-k metal gate transistor 160 subject to measurement by the methods and systems described herein.

In yet another non-limiting example illustrated in FIG. 5, parameters of interest of a high-k metal gate transistor 160 are measured based on combined analysis of x-ray and optical measurements. In the depicted example, the SiGe concentrations of the source 162 and the drain 163 of silicon substrate 161 are measured using XRF while the critical dimensions of the metal-gate electrode 165 and the thickness of the gate dielectric 164 can be measured with optical technologies such as spectroscopic ellipsometry.

In yet another non-limiting example, XRD is employed to measure the composition and stress of III-V materials. These parameters are fed forward in an analysis of optical measurements, such as spectroscopic ellipsometry, to determine thickness and critical dimension.

In some embodiments, a combined x-ray and optical analysis as described herein is implemented as part of a fabrication process tool. Examples of fabrication process tools include, but are not limited to, lithographic exposure tools, film deposition tools, implant tools, and etch tools. In this manner, the results of a combined x-ray and optical analysis are used to control a fabrication process. In one example, x-ray and optical measurement data collected from one or more targets is sent to a fabrication process tool. The x-ray and optical measurement data is analyzed as described herein and the results used to adjust the operation of the fabrication process tool.

As described herein, the term "critical dimension" includes any critical dimension of a structure (e.g., bottom critical dimension, middle critical dimension, top critical dimension, sidewall angle, grating height, etc.), a critical dimension between any two or more structures (e.g., distance between two structures), and a displacement between two or more structures (e.g., overlay displacement between overlaying grating structures, etc.). Structures may include three dimensional structures, patterned structures, overlay structures, etc.

As described herein, the term "critical dimension application" or "critical dimension measurement application" includes any critical dimension measurement.

As described herein, the term "metrology system" includes any system employed at least in part to characterize a specimen in any aspect, including critical dimension applications and overlay metrology applications. However, such terms of art do not limit the scope of the term "metrology system" as described herein. In addition, the metrology system 100 may be configured for measurement of patterned wafers and/or unpatterned wafers. The metrology system may be configured as a LED inspection tool, solar inspection tool, edge inspection tool, backside inspection tool, macro-inspection tool, or multi-mode inspection tool (involving data from one or more platforms simultaneously), and any other metrology or inspection tool that benefits from the calibration of system parameters based on critical dimension data.

Various embodiments are described herein for a semiconductor processing system (e.g., an inspection system or a lithography system) that may be used for processing a specimen. The term "specimen" is used herein to refer to a wafer, a reticle, or any other sample that may be processed (e.g., printed or inspected for defects) by means known in the art.

As used herein, the term "wafer" generally refers to substrates formed of a semiconductor or non-semiconductor material. Examples include, but are not limited to, monocrystalline silicon, gallium arsenide, and indium phosphide. Such substrates may be commonly found and/or processed in semiconductor fabrication facilities. In some cases, a wafer may include only the substrate (i.e., bare wafer). Alternatively, a wafer may include one or more layers of different materials formed upon a substrate. One or more layers formed on a wafer may be "patterned" or "unpatterned." For example, a wafer may include a plurality of dies having repeatable pattern features.

A "reticle" may be a reticle at any stage of a reticle fabrication process, or a completed reticle that may or may not be released for use in a semiconductor fabrication facility. A reticle, or a "mask," is generally defined as a substantially transparent substrate having substantially opaque regions formed thereon and configured in a pattern. The substrate may include, for example, a glass material such as amorphous $SiO_2$. A reticle may be disposed above a resist-covered wafer during an exposure step of a lithography process such that the pattern on the reticle may be transferred to the resist.

One or more layers formed on a wafer may be patterned or unpatterned. For example, a wafer may include a plurality of dies, each having repeatable pattern features. Formation and processing of such layers of material may ultimately result in completed devices. Many different types of devices may be formed on a wafer, and the term wafer as used herein is intended to encompass a wafer on which any type of device known in the art is being fabricated.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

Although certain specific embodiments are described above for instructional purposes, the teachings of this patent document have general applicability and are not limited to the specific embodiments described above. Accordingly, various modifications, adaptations, and combinations of various features of the described embodiments can be practiced without departing from the scope of the invention as set forth in the claims.

What is claimed is:

1. A model building and analysis engine comprising:
    a geometric model building module configured to generate a geometric model of a structure of a specimen;
    an optical response function building module configured to generate an optical response model of a response of the structure of the specimen to incident optical radiation based at least in part on the geometric model;
    an x-ray response function building module configured to generate an x-ray response model of a response of the structure of the specimen to incident x-ray radiation based at least in part on the geometric model;
    an x-ray data analysis module configured to receive a first amount of measurement data indicative of an amount of x-ray radiation detected from the specimen in response to an x-ray illumination beam incident on the specimen and directly determine a first specimen parameter value based on the received measurement data; and
    a fitting analysis module configured to:
        receive a second amount of measurement data indicative of an amount of optical radiation detected from the specimen in response to an optical illumination beam incident on the specimen;
        receive the first amount of measurement data indicative of the amount of x-ray radiation detected from the specimen in response to the x-ray illumination beam incident on the specimen;
        receive the at least one specimen parameter value from the x-ray data analysis module;
        determine a second specimen parameter value based on a fitting of the optical response model with the second amount of measurement data and a fitting of the x-ray response model to the first amount of measurement data; and
        output the second specimen parameter value for storage in a memory.

2. The model building and analysis engine of claim 1, wherein both the optical response model and the x-ray response model include at least one common geometric parameter from the geometric model.

3. The model building and analysis engine of claim 1, wherein the first specimen parameter value is any of a volume of the structure of the specimen, a thickness of the structure of the specimen, and an elemental composition of the structure of the specimen.

4. The model building and analysis engine of claim 2, wherein a value of the at least one common geometric parameter is determined based on the fitting of the x-ray response model to the first amount of measurement data and the determined value is treated as a constant in the fitting of the optical response model with the second amount of measurement data.

5. The model building and analysis engine of claim 2, wherein the at least one common geometric parameter is treated as a global parameter in a parallel fitting analysis including both the fitting of the optical response model with the second amount of measurement data and the fitting of the x-ray response model to the first amount of measurement data.

6. The model building and analysis engine of claim 1, wherein the fitting of the optical response model with the second amount of measurement data involves minimizing a cost function.

7. The model building and analysis engine of claim 5, wherein the parallel fitting analysis involves minimizing a combined cost function.

8. The model building and analysis engine of claim 2, wherein the at least one common geometric parameter is any of a line edge roughness, line width roughness, pore size, pore density, side wall angle, profile, film thickness, critical dimension, and pitch.

9. The model building and analysis engine of claim 1, wherein the model building and analysis engine is a computing system of a combined x-ray/optical metrology tool.

10. The model building and analysis engine of claim 9, wherein the combined x-ray/optical metrology tool comprises:
an x-ray illumination system including an x-ray illumination source and x-ray illumination optics configured to shape and direct an incident x-ray beam to an inspection area of a specimen;
an x-ray detector configured to detect the amount of x-ray radiation from the specimen in response to the incident x-ray beam;
an optical illumination system including an optical illumination source and optical illumination optics configured to shape and direct an incident optical illumination beam to the inspection area of the specimen simultaneous with the incident x-ray beam, wherein the incident optical illumination beam and the incident x-ray beam spatially overlap at the inspection area of the specimen; and
an optical detector configured to detect the amount of optical radiation from the specimen in response to the incident optical illumination beam.

11. A method comprising:
illuminating a structure of a specimen with an x-ray illumination beam;
detecting a first amount of measurement data indicative of an amount of x-ray radiation detected from the specimen in response to the x-ray illumination beam incident on the specimen;
illuminating the structure of the specimen with an optical illumination beam;
detecting a second amount of measurement data indicative of an amount of optical radiation detected from the specimen in response to the optical illumination beam incident on the specimen;
generating a geometric model of a structure of a specimen with a geometric model building module;
generating an optical response model based at least in part on the geometric model with an optical response function building module and an x-ray response model based at least in part on the geometric model with an x-ray response function building module;
determining directly a first specimen parameter value based on the first amount of measurement data with an x-ray data analysis module;
determining a second specimen parameter value based on the first specimen parameter value, a fitting analysis of the first amount of measurement data with the x-ray response model, and a fitting analysis of the second amount of measurement data with the optical response model with a fitting analysis module; and
storing the second specimen parameter value.

12. The method of claim 11, wherein the first specimen parameter value is any of a volume of the structure of the specimen, a thickness of the structure of the specimen, and an elemental composition of the structure of the specimen.

13. The method of claim 11, wherein the determined first specimen parameter value is treated as a constant in the fitting analysis of the first amount of measurement data with the x-ray response model, and the fitting analysis of the second amount of measurement data with the optical response model.

14. The method of claim 11, wherein both the optical response model and the x-ray response model include at least one common geometric parameter from the geometric model.

15. The method of claim 14, wherein the determining the second specimen parameter value involves determining a value of the at least one common geometric parameter based on the fitting analysis of the first amount of measurement data, and wherein the determined value of the at least one common geometric parameter is treated as a constant in the fitting analysis of the second amount of measurement data.

16. The method of claim 14, wherein the determining the second specimen parameter value involves determining a value of the at least one common geometric parameter based on a parallel fitting analysis of the first amount of measurement data with the x-ray response model and the second amount of measurement data with the optical response model.

17. The method of claim 11, further comprising:
determining a residual value of a cost function associated with the fitting analysis of the first amount of measurement data with the x-ray response model and the fitting analysis of the second amount of measurement data with the optical response model;
determining if the residual value exceeds a predetermined threshold value;
restructuring the geometric model of the structure of the specimen if the residual value exceeds the predetermined threshold value; and
storing the geometric model of the structure of the specimen if the residual value does not exceed the predetermined threshold value.

18. A metrology system, comprising:
an x-ray illumination source configured to illuminate a structure of a specimen with an x-ray illumination beam;
an x-ray detector configured to detect a first amount of measurement data indicative of an amount of x-ray radiation detected from the specimen in response to the x-ray illumination beam incident on the specimen;
an optical illumination system configured to illuminate the structure of the specimen with an optical illumination beam;
an optical detector configured to detect a second amount of measurement data indicative of an amount of optical radiation detected from the specimen in response to the optical illumination beam incident on the specimen; and
a non-transitory, computer-readable medium comprising:
code for causing a computer to generate a geometric model of a structure of a specimen;
code for causing the computer to generate an optical response model and an x-ray response model based at least in part on the geometric model;
code for causing the computer to receive the first amount of measurement data;
code for causing the computer to determine directly a first specimen parameter value based on the received first amount of measurement data;
code for causing the computer to receive the second amount of measurement data;
code for causing the computer to determine a second specimen parameter value based on the first specimen parameter value, a fitting analysis of the first amount of measurement data with the x-ray response model, and a fitting analysis of the second amount of measurement data with the optical response model; and code for causing the computer to store the second specimen parameter value.

19. The metrology system of claim 17, wherein the determined first specimen parameter value is treated as a constant in the fitting analysis of the first amount of measurement data with the x-ray response model, and the fitting analysis of the second amount of measurement data with the optical response model.

20. The metrology system of claim 17, the non-transitory, computer-readable medium further comprising:

code for causing the computer to determine a residual value of a cost function associated with the fitting analysis of the first amount of measurement data with the x-ray response model and the fitting analysis of the second amount of measurement data with the optical response model;

code for causing the computer to determine if the residual value exceeds a predetermined threshold value;

code for causing the computer to restructure the geometric model of the structure of the specimen if the residual value exceeds the predetermined threshold value; and code for causing the computer to store the geometric model of the structure of the specimen if the residual value does not exceed the predetermined threshold value.

\* \* \* \* \*